US008822483B2

(12) United States Patent
McQuade et al.

(10) Patent No.: US 8,822,483 B2
(45) Date of Patent: *Sep. 2, 2014

(54) SIX-MEMBERED N-HETEROCYCLIC CARBENE-BASED CATALYSTS FOR ASYMMETRIC REACTIONS

(75) Inventors: D. Tyler McQuade, Tallahassee, FL (US); Jin Kyoon Park, Tallahassee, FL (US); Matthew D. Rexford, Tallahassee, FL (US); Hershel H. Lackey, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 203 days.

This patent is subject to a terminal disclaimer.

(21) Appl. No.: 13/477,222

(22) Filed: May 22, 2012

(65) Prior Publication Data
US 2012/0302434 A1 Nov. 29, 2012

Related U.S. Application Data

(62) Division of application No. 12/870,901, filed on Aug. 30, 2010, now Pat. No. 8,222,265.

(60) Provisional application No. 61/238,367, filed on Aug. 31, 2009.

(51) Int. Cl.
| | | |
|---|---|---|
| A61K 31/519 | (2006.01) | |
| C07D 487/04 | (2006.01) | |
| C07F 1/08 | (2006.01) | |
| B01J 31/40 | (2006.01) | |
| C07F 5/02 | (2006.01) | |
| B01J 31/22 | (2006.01) | |

(52) U.S. Cl.
CPC ............... *C07F 1/08* (2013.01); *C07D 487/04* (2013.01); *B01J 2531/16* (2013.01); *B01J 2231/323* (2013.01); *C07F 5/025* (2013.01); *B01J 31/2273* (2013.01); *B01J 31/2269* (2013.01)
USPC .......................................... 514/267; 544/250

(58) Field of Classification Search
CPC ....... A61K 31/519; C07D 487/04; C07F 1/08
USPC .......................................... 514/267; 544/250
See application file for complete search history.

(56) References Cited

U.S. PATENT DOCUMENTS 8,222,265 B2 * 7/2012 McQuade et al. ............ 514/267

OTHER PUBLICATIONS

Smith, M. B. Organic Synthesis, McGraw-Hill, Inc. 1994, Chapter 1.*
Ali, H. A., et al., *Organometallics*, 20:3962 (2001).
Baskakov, D., et al., *Organometallics*, 26:626 (2007) (biisoquinoline core).
Bazinet, P., et al., *J. Am. Chem. Soc.*, 125:13314 (2003).
Bell, N. J., et al., *Chem. Commun.*, 1854 (2004).
Binobaid, A., et al., *Dalton Trans.*, pp. 7099 (2009).
Busacca, C. A., et al., *Org. Lett.*, 10:341 (2008).
Cavell, K. J., et al., *Dalton Trans.*, 4922 (2006) (biisoquinoline core).
Cesar, V. et al., *J. Am. Chem. Soc.* 130:11286 (2008).
Chen, I.-H. Et al., *J. Am. Chem. Soc.*, 131:11664 (2009).
Dang, L., et al., *Chem. Commun.*, 3987 (2009).
Dang, L., et al., *Organometallics*, 27:4443 (2008).
Davis, E. M., et al., *Org. Process Res. Dev.*, 9:843 (2005).
Enders, D., et al., *Chem. Rev.*, 107:5606 (2007).
Fleming, W. J., et al., *Org. Biomol. Chem.*, 7:2520 (2009).
Glorius, F., et al., *Chem. Commun.*, 2704 (2002) (oxazoline core).
Godeau, J., et al., *Electrochim. Acta*, 54:5116 (2009).
He, M., et al., *J. Am. Chem. Soc.*, 130:418 (2008).
Hirano, K., et al., *Org. Lett.*, 9:5031 (2007) (Ni catalyzed reactions).
Ito, H., et al., *Tetrahedron Lett.*, 41:6821 (2000).
Kabalka, G. W., et al., *Tetrahedron Lett.*, 43:2323 (2002) (Rh catalyzed reactions).
Kolychev, E. L. et al., *J. Organomet. Chem.*, 694:2454 (2009).
Laitar, D. S., et al., *J. Am. Chem. Soc.*, 127:17196-17197 (2005).
Lavallo, V., et al., *Angew. Chem., Int. Ed. Engl.*, 44:5705 (2005).
Lawson, Y. G., et al., *Chem. Commun.*, 2051 (1997) (Pt catalyzed reactions).
Lee, J.-E., et al., *Angew. Chem., Int. Ed.*, 47:145 (2008).
Lee, J.-E., et al., *Chem. Commun.*, 733 (2008).
Lee, K.-S. Et al., *J. Am. Chem. Soc.*, 131:7253 (2009).
Lee, Y., et al., *J. Am. Chem. Soc.*, 131:3160 (2009).
Lillo, V., et al., *Dalton Trans.*, 2899 (2009).
Lillo, V., et al., *Organometallics*, 28:659 (2009).

(Continued)

*Primary Examiner* — Erich A Leeser
(74) *Attorney, Agent, or Firm* — Alchemy-Partners, PC

(57) ABSTRACT

The present invention provides a catalyst complex or ligand, and compositions thereof, for use in a variety of organic reactions having high reactivity and enantioselectivity. The catalyst is a N-heterocyclic carbene having three fused rings with first and second rings being six-membered rings and the third being a five-membered ring. The first ring is fused to the second and has four substituents. The second ring has two nitrogens flanking a carbene atom with one nitrogen bound to a substituent. The carbene atom may optionally be bonded to a metal. The third ring is fused to the second ring and contains two nitrogens. The third ring of the catalyst has a double bond and two substituents on adjacent non-fused carbons. A non-fused nitrogen of the third ring is partially bonded to another substituent. Methods for the synthesis and use of the catalyst embodiments of the present invention are also provided.

36 Claims, 11 Drawing Sheets

(56) References Cited

OTHER PUBLICATIONS

Lloyd-Jones, G. C., et al., *Chem.-Eur. J.*, 12:5361 (2006).
Marion, N., et al., *Angew. Chem., Int. Ed. Engl*, 46:2988 (2007).
Mayr, M., et al., *Chem. Eur. J.*, 10:1256 (2004).
Metallinos, C., et al., *Organometallics*, 28:1233 (2009) (phenanthroline core).
Mun, S., et al., *Org. Lett.*, 8:4887 (2006).
Prasang, C., et al., *J. Am. Chem. Soc.*, 127:10182 (2005).
Reynolds, N. T.; Rovis, T. *J. Am. Chem. Soc.*, 127:16406.
Scarborough, C. C., et al., *Dalton Trans.*, 2284 (2009) (biphenyl core).
Scarborough, C. C., et al., *Tetrahedron*, 65:5084 (2009) (biphenyl core).
Schiffner, J. A., et al., *Angew. Chem., Int. Ed.*, 49:1194 (2010).
Seo, H., et al., *J. Org. Chem.*, 73:1983 (2008) (biisoquinoline core).
Sim, H.-S., et al., *Chem. Eur. J.*, 15:1939 (2009).
Takahashi, K. et al., *J. Organomet. Chem.*, 625:47 (2001).
Tu, T., et al., *Adv. Synth. Catal.*, 351:1029 (2009).
Park, J.K., et al., *Organic Letters*, vol. 12, No. 21, 5008-5011 (2010).

\* cited by examiner

| Entry | Solvent | Temp(°C) | Time | Yield (%)[b] | ee (%)[c,d] |
|---|---|---|---|---|---|
| 1 | Et$_2$O | 0 | <1min | >98 | 78 |
| 2 | Et$_2$O | −30 | 3h | >98 | 82 |
| 3 | Et$_2$O | −55 | 6h | >98 | 86 |
| 4 | Toluene | 0 | <1min | >98 | 78 |
| 5 | THF | 0 | <1min | >98 | 69 |
| 6 | CH$_3$CN | 0 | <1min | >98 | 63 |
| 7 | CH$_2$Cl$_2$ | 0 | <1min | >98 | 64 |

| Entry | Substrate | Yield (%)[b] | ee (%)[c] |
|---|---|---|---|
| 1 | (crotonate) OtBu | 93 (92[g], 91[h]) | 90 (R) (86[g], 88[h]) |
| 2 | (pentenoate) OEt | 92 | 90 |
| 3 | (octenoate) OEt | 90 | 91 |
| 4 | (isopropyl acrylate) OEt | 91 | 96 (S) |
| 5 | (cyclohexyl acrylate) OEt | 95 | 90 |
| 6 | (ethyl-branched) OEt | 95 | 90 |
| 7[d,e] | (cinnamate) OMe | 88 (87[g], 88[h]) | 87 (85[g](S), 80[h]) |
| 8[d,e] | (p-methyl cinnamate) OiBu | 91 | 82 |
| 9[d,f] | (o-methyl cinnamate) OiBu | 95 (93[g]) | 96 (92[g](S)) |
| 10[d,f] | (o-methoxy cinnamate) OiBu | 90 | 92 |

| Entry | Ester | Mol% | Time | Conv.(%)[d] | ee(%) | TON |
|---|---|---|---|---|---|---|
| 1[a] | 44mg | 10 | <1min | >99 | 92 | 10 |
| 2[a] | 44mg | 1 | <1min | >99 | 91 | 100 |
| 3[b] | 0.44g | 0.1 | 3min | >99 | 88 | 1,000 |
| 4[b] | 0.44g | 0.05 | 80min | >99 | 87 | 2,000 |
| 5[c] | 2.0g | 0.01 | 100min | >99 | 88 | 10,000 |

| Entry | Catalyst | Temp. | Time | Ratio[b] (5a/5b) | Yield[c] (%) |
|---|---|---|---|---|---|
| 1 | 1 (1 mol%) | −20 °C | 10 min | >25/1 | 88 (5a) (70) |
| 2 | 2 (1 mol%) | −20 °C | 20 min | <1/24 | 88 (5b) (71) |
| 3[d] | 3 (3 mol%) | rt | 6 h | 1/1.5 | 65 (5a+5b) (16)[e] |

FIG.12E

| Entry | Substrate | Temp. | Reaction time | Yield (%)[a] |
|---|---|---|---|---|
| 1 | Ph-CH=CH-C(O)OEt | rt | 2 h | 99 % |
| 2 | HO-C6H4-CH=CH-C(O)OEt | rt | 5 h | 68 % |

FIG.13

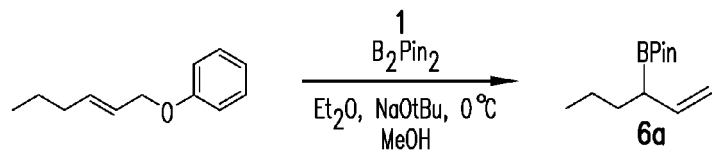
FIG.14A
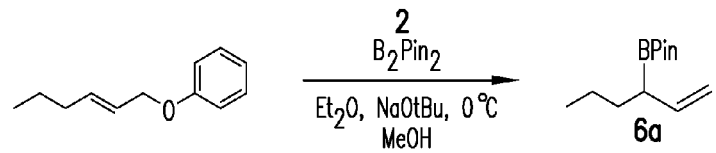
FIG.14B
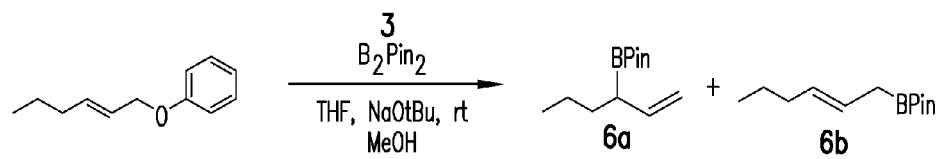
FIG.14C
| Entry | Catalyst (mol%) | Time | 6a/6b[b] | Yield (%)[c] |
|---|---|---|---|---|
| 1 | 1 (1 mol%) | 20 min | >99/1 | 91 % (86 %)[d] |
| 2 | 2 (1 mol%) | 3 h | >99/1 | 17 % |
| 3[e] | 3 (3 mol%) | 22 h | 14/1 | 11 % |
FIG.14D

SIX-MEMBERED N-HETEROCYCLIC CARBENE-BASED CATALYSTS FOR ASYMMETRIC REACTIONS

CROSS-REFERENCE TO RELATED APPLICATIONS

This application is a Divisional application and claims the benefit of and the priority from U.S. patent application Ser. No. 12/870,901, filed Aug. 30, 2010, and U.S. Provisional patent application No. 61/238,367, filed Aug. 31, 2009, which is incorporated herein by reference.

GOVERNMENT INTEREST STATEMENT

The United States Government has rights in this invention pursuant to National Science Foundation (NSF) Grant No. CHE-0809261.

BACKGROUND

1. Field of the Invention

The present invention relates to the field of asymmetrical catalysts used for transition formations in a wide variety of organic synthesis reactions.

2. Related Art

Asymmetric catalysis is a mainstay of the pharmaceutical discovery and manufacturing process. Asymmetric catalysts are often transition metal-based compounds, and the ligands associated with the metal are often difficult and expensive to synthesize. There continues to be a need in the art for new and improved asymmetric catalysts that are highly active, stereoselective and less expensive to synthesize.

SUMMARY

According to a first broad aspect of the present invention, a chemical compound is provided having a first, second and third fused rings and the following structural formula:

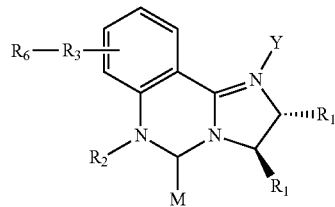

wherein each $R_1$ group bound to the third ring is one of the following: alkyl, vinyl, allyl, alkynyl, or aryl, wherein the $R_2$ group bound to the second ring is one of the following: alkyl, vinyl, allyl, alkynyl, or aryl, wherein each of the $R_3$, $R_4$, $R_5$, and $R_6$ groups bound to the first ring is one of the following: alkyl, vinyl, allyl, alkynyl, aryl, alkoxy, amino, carbonyl, carbamoyl, proteo, deutero, halo, hydroxyl, thioether, thiocarbonyl, urea, or thiourea, wherein the M group comprises a metal atom, wherein the Y group is either a lone pair of electrons or a coordinating Lewis acid, and wherein the carbon atom positioned between the nitrogens of the second ring and bonded to the M group is a carbene atom.

According to a second broad aspect of the present invention, a chemical compound is provided having a first, second and third fused rings and the following structural formula:

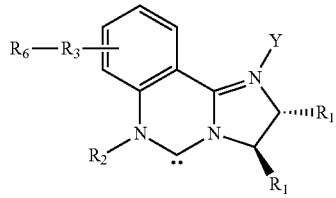

wherein each $R_1$ group bound to the third ring is one of the following: alkyl, vinyl, allyl, alkynyl, or aryl, wherein the $R_2$ group bound to the second ring is one of the following: alkyl, vinyl, allyl, alkynyl, or aryl, wherein each of the $R_3$, $R_4$, $R_5$, and $R_6$ groups bound to the first ring is one of the following: alkyl, vinyl, allyl, alkynyl, aryl, alkoxy, amino, carbonyl, carbamoyl, proteo, deutero, halo, hydroxyl, thioether, thiocarbonyl, urea, or thiourea, wherein the Y group is a coordinating Lewis acid, and wherein the carbon atom positioned between the nitrogens of the second ring is a carbene atom.

According to a second broad aspect of the present invention, a method is provided for the making/synthesis of catalyst embodiments of the present invention. The 6-NHC catalyst embodiments of the present invention may be synthesized according to any method(s) described herein and/or by any method(s) known in the art.

According to a third broad aspect of the present invention, a method of using the compounds or compositions of the present invention are also provided according to any method known in the art and/or described herein and may involve one of the following reaction types: β-functionalization; allylic substitution; and hydroboration of alkynes. According to some embodiments, a method is provided comprising the step of reacting a substrate in a β-functionalization reaction in the presence of a catalyst to produce a product, wherein the substrate is a molecule having a double bond between two carbon atoms, wherein one of those carbons is bonded to an electron withdrawing group (EWG) and the other carbon is bonded to a variable substituent or group, wherein the catalyst is as described herein, and wherein the product of the β-functionalization reaction has an enantiomeric excess of about 75% or greater. According to some embodiments, the methods may further comprise the step of isolating or purifying the product of the reacting step and/or measuring the product of the reacting step.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 12E is a table summarizing the enantioselectivity comparison data for the different catalysts in β-borylation reactions;

FIG. 13 is a table showing the results for validation of reaction conditions for a xantphos catalyzed reaction;

FIG. 14A is an allylic substitution reaction for testing the enantioselectivity of a catalyst embodiment of the present invention (1);

FIG. 14B is an allylic substitution reaction for testing the enantioselectivity of another catalyst (2) for comparison;

FIG. 14C is an allylic substitution reaction for testing the enantioselectivity of another catalyst (3) for comparison; and FIG. 14D is a table summarizing the enantioselectivity comparison data for the different catalysts in allylic substitution reactions.

DETAILED DESCRIPTION

Definitions

Figure 1A:
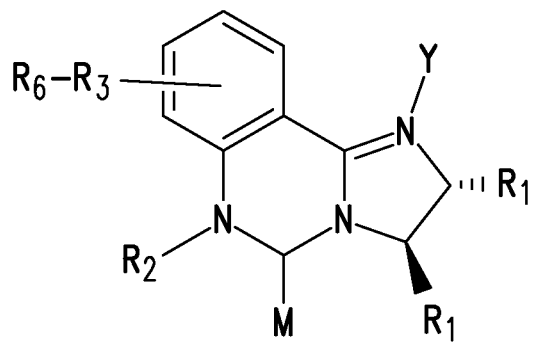
FIG. 1A is a general structural formula of the 6-NHC metal-complex catalyst according to embodiments of the present invention.

Where the definition of terms departs from the commonly used meaning of the term, applicant intends to utilize the definitions provided below, unless specifically indicated.

For purposes of the present invention, the term "asymmetric catalyst" refers to a catalyst that is enantioselective and/or stereoselective in terms of the products generated by an organic reaction. Such an asymmetric catalyst may be one that causes an enantiomeric excess of products of an organic reaction.

For purposes of the present invention, the term "stereoisomers" refer to two or more molecules having the same molecular formula but differ in their three-dimensional orientation of atoms.

For purposes of the present invention, the term "enantiomers" refer to stereoisomers that are mirror images of each other in structure (i.e., cannot be superimposed).

For purposes of the present invention, the term "chirality" refers to the property of a molecule that is not superimposable in three dimensions on its mirror image. Chirality may be due to "point chirality" present in relation to one atom of a molecule, such as a carbon atom. Point chirality at a carbon atom may exist when there are four different groups or substituents bound to the carbon atom. There may be multiple chiral atoms within a molecule.

For purposes of the present invention, the terms "enantioselective" and "enantioselectivity" refer to the property of favoring one enantiomer as a product of a reaction over another. Enantioselectivity may be due at least in part to the presence of a catalyst that encourages a particular enantiomer as a product of a reaction.

For purposes of the present invention, the terms "enantiomeric excess," "ee" or "e.e." refer to the absolute difference between the mole fraction of each enantiomer products of a reaction. The enantiomeric excess may be expressed in terms of a fraction or percentage with the total of the mole fractions of the two enantiomer products equaling either 1.0 or 100%, respectively.

For purposes of the present invention, the terms "N-heterocyclic carbene" or "NHC" refer to a molecule having a carbene atom present in a heterocyclic ring where at least one of the atoms flanking the carbene carbon is a nitrogen.

For purposes of the present invention, the term "carbene" refers a carbon atom six total valence electrons where four electrons are shared to form bonds with two other neighboring atoms and where two electrons are present as a lone pair. The lone pair can exist in two states where both electrons in the lone pair are in the same orbital (singlet) or both electrons in the lone pair are found in different orbitals (triplet).

For purposes of the present invention, the term "fused" in reference to chemical structures and compounds refer to two or more rings that share a bond of the respective rings.

For purposes of the present invention, the term "substrate" refers to a molecule or compound that is modified by an organic reaction, such as β-functionalization, allylic substitution or hydroboration of alkynes, in the presence of a catalyst of the present invention.

For purposes of the present invention, the term "catalyst" may refer to a substance, molecule or compound that increases the rate of a reaction. According to some embodiments, the catalyst may include a 6-NHC metal complex or ligand, which may also increase the yield per time and/or the enantioselectivity of the reaction.

Description

N-heterocyclic carbenes (NHC) are an important chemical class showing excellent properties when used as components of, or directly as, catalysts. NHC-Metal complexes are generally outstanding catalysts for a wide range of organic transition formations. The majority of active NHC complexes are comprised of structures where the carbene resides on a five-membered ring (5-NHC). Non-five membered ring systems are rare. Only a few examples exist where ligands based on seven-membered rings have exhibited promising activity compared to other ligand classes. Beyond five- and seven-membered rings, the literature is even sparser. Few six-membered ring NHCs (6-NHCs) are known. Of this small subset of 6-NHCs, only a few transition metal catalysts have been prepared, and none are asymmetric catalysts although they show improved properties over 5-NHCs. See, e.g., Binobaid, A., et al., *Dalton Trans., pp.* 7099 (2009); Tu, T., et al., *Adv. Synth. Catal.,* 351:1029 (2009); and Mayr, M., et al., *Chem. Eur. J.,* 10:1256 (2004), the entire contents and disclosures of which are hereby incorporated by reference. Despite the fact that 6-NHCs have yet to produce a wide range of catalysts, these NHCs offer unique structural features including unique electronic and steric properties and the potential for greater modularity stemming from the extra carbon atom. See, e.g., Kolychev, E. L. et al., *J. Organomet. Chem.,* 694:2454 (2009); Cesar, V. et al., *J. Am. Chem. Soc.* 130:11286 (2008); Lloyd-Jones, G. C., et al., *Chem.-Eur. J.,* 12:5361 (2006); Prasang, C., et al., *J. Am. Chem. Soc.,* 127:10182 (2005); Lavallo, V., et al., *Angew. Chem., Int. Ed. Engl.,* 44:5705 (2005); and Bazinet, P., et al., *J. Am. Chem. Soc.,* 125:13314 (2003), the entire contents and disclosures of which are hereby incorporated by reference.

Surprisingly, in contrast to organocatalytic carbenes, no fused tricyclic NHC-metal catalysts with rigid chiral groups have exhibited high enantioselectivity. See, e.g., He, M., et al., *J. Am. Chem. Soc.,* 130:418 (2008); Enders, D., et al., *Chem. Rev.,* 107:5606 (2007); Marion, N., et al., *Angew. Chem., Int. Ed. Engl,* 46:2988 (2007); Reynolds, N. T.; Rovis, T. *J. Am. Chem. Soc.,* 127:16406; Scarborough, C. C., et al., *Tetrahedron,* 65:5084 (2009) (biphenyl core); Scarborough, C. C., et al., *Dalton Trans.,* 2284 (2009) (biphenyl core); Metallinos, C., et al., *Organometallics,* 28:1233 (2009) (phenanthroline core); Seo, H., et al., *J. Org. Chem.,* 73:1983 (2008) (biisoquinoline core); Baskakov, D., et al., *Organometallics,* 26:626 (2007) (biisoquinoline core); Cavell, K. J., et al., *Dalton Trans.,* 4922 (2006) (biisoquinoline core); Glorius, F., et al., *Chem. Commun.,* 2704 (2002) (oxazoline core), the entire contents and disclosures of which are hereby incorporated by reference in their entirety. Recognizing the strengths of both 6-NHCs and annulated NHCs, we have discovered and designed a new 6-NHC ligand and ligand-metal catalyst that is relatively easy to prepare and shows excellent activity and enantioselectivity.

According to a first broad aspect of the present invention, a 6-NHC catalyst compound and any compositions comprising a 6-NHC catalyst compound are provided. Compositions of the present invention may include, for example, a reaction mixture or solution comprising the 6-NHC catalyst compound of the present invention as described herein. According to embodiments of the present invention, a compound is provided as shown in FIG. 1A having at least three fused rings with two of the rings being six-membered rings and the third being a five-membered ring. The first ring of the catalyst is a benzene ring having four substituents ($R_3$-$R_6$) bound to the carbons of the first ring that are not fused to a second ring. A second middle ring of the catalyst is a six-membered ring having two nitrogens directly flanking a carbene atom and fused to the first ring. In addition, a substituent ($R_2$) may be bound to the nitrogen of the second ring of the catalyst that is not fused to any other ring. Finally, a third five-membered ring of the catalyst is fused to the second ring. The third ring of the catalyst contains two nitrogens with one of the nitrogens shared or fused with the second ring and the other nitrogen adjacent to the carbon fused to the second ring. In addition, the third ring has a double bond between the fused carbon and the non-fused nitrogen. The third ring also has two substituents (each $R_1$) on the adjacent non-fused carbon atoms of the third ring arranged either in cis or in trans relative to the third ring. According to some embodiments, the non-fused nitrogen atom of the third ring of the catalyst may also be associated with, or partially bonded to, another substituent (Y).

Figure 1B:
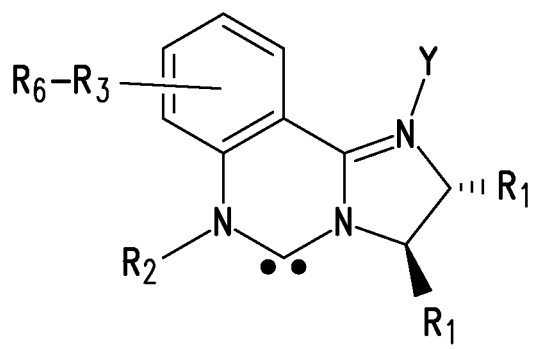
FIG. 1B is a general structural formula of the 6-NHC ligand catalyst according to embodiments of the present invention.

According to these embodiments, the $R_3$ through $R_6$ substituents or groups bound to the first ring of the catalyst may each be any one of the following: alkyl, vinyl, allyl, alkynyl, aryl, alkoxy, amino, carbonyl, carbamoyl, proteo, deutero, halo, hydroxyl, thioether, thiocarbonyl, urea, or thiourea. Furthermore, each of the $R_1$ and $R_2$ substituents or groups bound to the third and second rings of the catalyst, respectively, may be any one of the following: alkyl, vinyl, allyl, alkynyl, or aryl. As stated above, the Y substituent of the catalyst may associate with, or be partially bonded to, the non-fused nitrogen atom of the third ring. The Y substituent may be either a lone pair of electrons or any coordinating Lewis acid, such as any alkali or alkaline earth metal cations, any transition metal ions or electron poor main group elements such as boron- or aluminum-containing compounds. According to embodiments of the present invention, the two adjacent carbon atoms of the third ring of the catalyst that are not fused to the second ring may each have point chirality with one $R_1$ substituent above and the other below the third ring. The $R_2$ substituent may have a steric effect, hindrance and/or blockade when compounds of the present invention are used as a catalyst. According to some embodiments, the carbene atom of the catalyst may be bonded to a metal (M). Alternatively, however, the 6-NHC catalyst of the present invention may instead exist as a ligand having two unbound (free) valence electrons in either a spin paired (singlet) or a non-spin paired (triplet) arrangement (See FIG. 1B). If the carbene atom of the 6-NHC catalyst of the present invention is bound to a metal (M), then such a metal may generally include any transition metal (i.e., any metal in the d-block or Groups 3-12 of the periodic table) or main group metal (i.e., any metal in Groups 1 and 2 or 13-16 of the periodic table). In addition, such a metal (M) may also include any compound or salt of such metals, such as copper (I) chloride (CuCl) or any other metal in a non-zero oxidation state.

According to a second broad aspect of the present invention, methods are provided for the making/synthesis of a catalyst embodiment(s) of the present invention. According to some embodiments, the 6-NHC catalyst complexes or ligands of the present invention may be synthesized or made according to any method(s) described herein and/or by using any method(s) known in the art.

According to a third broad aspect of the present invention, methods of using the compounds or compositions of the present invention are also provided according to any method known in the art and/or described herein. The 6-NHC catalyst of the present invention may be used in a variety of chemical reactions for industrial and pharmaceutical applications due especially to its high activity and enantioselectivity as a catalyst in these reactions for transforming various substrate compounds. These reactions may be used, for example, to produce or synthesize a precursor or intermediate of a final end product. The catalyst of the present invention may be used, for example, in three different types of reactions: β-functionalization; allylic substitution; and hydroboration of alkynes. Indeed, reactivity has been demonstrated in many cases for these types of reactions.

According to embodiments of the present invention, the 6-NHC complexes or ligands of the present invention may be used as a catalyst in various organic reactions. According to these method of use embodiments, an appropriate substrate for the particular reaction type (e.g., β-functionalization, allylic substitution, or hydroboration of alkynes) may be combined, mixed, reacted, etc., with one or more of the following: a diboron-containing compound, a boron/silicon-containing compound, or a phosphorous/silicon-containing compound as described herein and a 6-NHC catalyst or ligand embodiment of the present invention. The reaction temperature, reaction time, substrate concentration, and/or catalyst concentration or Mol %, including any combination thereof, may be adjusted or controlled as described herein. The product(s) of such reactions may optionally be isolated, purified, etc., in a second step according to standard techniques and procedures, such as for use in a subsequent reaction. Isolation or purification may refer to increasing the purity and/or concentration of the product(s). The product(s) of such reactions may also be optionally measured or detected in a second step according to any standard technique, including NMR spectroscopy, chromatography, etc. The product(s) of such reactions may also have certain characteristics or properties, such as a particular yield and/or a particular range of steroselectivity or enantiomeric excess such as described herein.

According to some embodiments, the catalyst of the present invention may be used in a β-functionalization reaction, such as a β-borylation, β-silylation, or β-phosphorylation reaction. These reactions may be used, for example, to produce or synthesize a precursor or intermediate of a final end product. In the following examples of reactions utilizing the catalyst of the present invention, the attachment of the boron-containing, phosphorous-containing, or silicon-containing molecules to the substrate in the reaction product may be removed in a subsequent reaction, such as under oxidative conditions.

According to those embodiments in which the catalyst is used in a β-borylation reaction, the substrate of the reaction may generally include molecules having an acyclic or cyclic (exocyclic or endocyclic) double bond between two carbon atoms with one of those carbons bonded to an electron withdrawing group (EWG) and the other carbon bonded to another substituent or group ($R_1$; not to be confused with $R_1$ of the catalyst). The $R_1$ substituent of the substrate may generally be any group where the atom directly attached to the double bond is a carbon, such as any alkyl group, aryl group, etc., and the EWG of the substrate may generally include one of the following: ester, carboxylic acid, acid halide, amide, sulfone, nitro, nitrile, thioester, or thioamide.

Figure 2A:
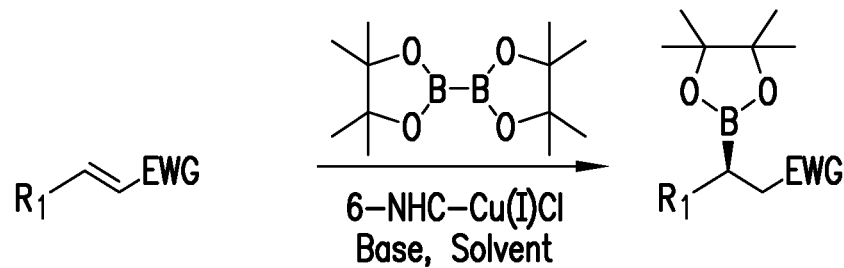
FIG. 2A is a model reaction for use of a catalyst embodiment of the present invention in a β-borylation of a substrate.

According to these embodiments as shown in FIG. 2A, the β-borylation reaction may proceed in the presence of the catalyst by bonding of a boron atom of a diboron-containing compound, such as Bis(pinacolato)diboron, Bis(catecholato) diboron, or any compound containing a boron-boron bond, to one of the two doubly bonded carbons and eliminating the double bond between the carbon atoms. The β-borylation reaction mixture may contain a solvent and a base. The amount of the catalyst of the present invention in the β-borylation reaction may have a Mol % in a range of about 0.01 to about 10.0, or alternatively in a range of about 0.1 to about 10.0. (Mole percent or Mol %=moles of catalyst/moles of starting material.) The amount of the catalyst of the present invention in the β-borylation reaction may depend on the amount of substrate in the reaction. The solvent for the β-borylation reaction may range from a non-polar solvent (for example, one or more of the following: diethyl ether, toluene, THF, or $CH_2Cl_2$) to polar aprotic solvents (for example, $CH_3CN$, DMF or DMSO), and the base may be an alkoxide base, such as sodium t-butoxide (NaOtBu), or nitrogenous base, such as lithium hexamethyldisilazide. The β-borylation reaction may be carried out at colder temperatures, such as in a range from about $-55°$ C. to about $0°$ C., or alternatively in a range from about $-30°$ C. to about $0°$ C., or alternatively in a range from about $-55°$ C. to about $-30°$ C. According to some embodiments, the temperature of the β-borylation reaction may be about $0°$ C. or greater.

According to some embodiments, the β-borylation reaction in the presence of the catalyst may have an enantiomeric excess (ee) or selectivity of product of about 75% or greater, 80% or greater, 85% or greater, or 90% or greater. In addition, the β-borylation reaction may be allowed to proceed long enough to allow near 100% yield, such as greater than 98% or 99% yield. The reaction time for reaching near 100% yield may vary depending on the amount of substrate and/or catalyst as well as temperature from, for example, about less than 1 minute to about 3 minutes, or alternatively to about 80 minutes, or alternatively to about 3 hours, or alternatively to about 6 hours, or any range therein. Generally, more time is required at lower temperatures and/or higher substrate concentrations, but the lower temperatures may allow for greater enantioselectivity.

Figure 2B:
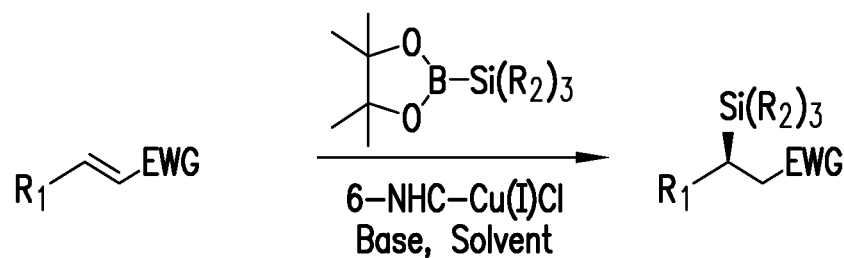
FIG. 2B is a model reaction for use of a catalyst embodiment of the present invention in a β-silylation of a substrate.

According to those embodiments in which the catalyst is used in a β-silylation reaction, the substrate of the reaction may generally be the same kinds of molecules described above for the β-borylation reaction. According to these embodiments as shown in FIG. 2B, the β-silylation reaction may proceed in the presence of the catalyst by bonding of a silicon atom of a boron/silicon-containing compound, such as 2-(Dimethylphenylsilyl)-1,3,2-benzodioxaborole, (Dimethylphenylsilyl) boronic acid pinacol ester, etc., to one of the two doubly bonded carbons and eliminating the double bond between the carbon atoms. According to these embodiments, the silicon of the boron/silicon-containing compound may be bonded to three substituents ($R_2$; not to be confused with $R_2$ of the catalyst). The $R_2$ substituent of the boron/silicon-containing compound may be an alkyl or aryl group. The β-silylation reaction mixture may contain a solvent and a base as described above for the β-borylation reaction. According to these embodiments, the Mol % of the catalyst, the temperature ranges, reaction times, enantiomeric excess (ee), and yield may be about the same for the β-silylation reaction as described above for the β-borylation reaction.

Figure 2C:
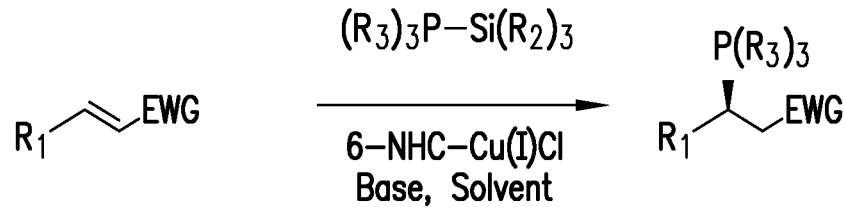
FIG. 2C is a model reaction for use of a catalyst embodiment of the present invention in a β-phosphorylation of a substrate.

According to those embodiments in which the catalyst is used in a β-phosphorylation reaction, the substrate of the reaction may generally be the same kinds of molecules described above for the β-borylation reaction. According to these embodiments as shown in FIG. 2C, the β-phosphorylation reaction may proceed in the presence of the catalyst by bonding of a phosphorous atom of a phosphorous/silicon-containing compound, such as (Diphenylphosphino)trimethylsilane, Diethyl trimethylsilylphosphate, etc., to one of the two doubly bonded carbons and eliminating the double bond between the carbon atoms. According to these embodiments, the phosphorous of the phosphorous/silicon-containing compound may be bonded to three substituents ($R_2$; not to be confused with $R_3$ of the catalyst). The $R_3$ substituent of the phosphorous/silicon-containing compound may be an alkyl, aryl or alkyoxy group. The β-phosphorylation reaction mixture may contain a solvent and a base as described above for the β-borylation reaction. According to these embodiments, the Mol % of the catalyst, the temperature ranges, reaction times, enantiomeric excess (ee), and yield may be about the same for the β-phosphorylation reaction as described above for the β-borylation reaction.

Figure 3:
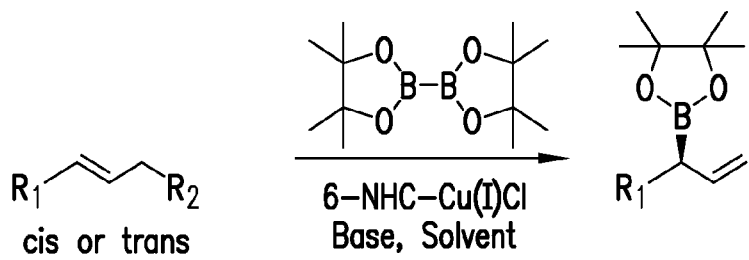
FIG. 3 is a model reaction for use of a catalyst embodiment of the present invention in an allylic substitution of a substrate.

According to those embodiments in which the catalyst is used in an allylic substitution reaction, the substrate of the reaction may generally include molecules having an acyclic or cyclic (exocyclic or endocyclic) double bond between a first carbon atom and a second carbon atom with the first carbon bonded to a first substituent or group ($R_1$; not to be confused with $R_1$ of the catalyst) and the second carbon bonded to a third carbon, which is bonded to a second substituent or group ($R_2$; not to be confused with $R_2$ of the catalyst). The $R_1$ substituent of the substrate may generally be any group where the atom directly attached to the double bond is a carbon, such as any alkyl group, aryl group, etc., and the $R_2$ substituent of the substrate may generally be any carbonate or aryloxy group. According to these embodiments as shown in FIG. 3, the allylic substitution reaction may proceed in the presence of the catalyst by bonding of a boron atom of a diboron-containing compound, such as Bis(pinacolato)diboron, Bis(catecholato)diboron, or any compound containing a boron-boron bond, to the first carbon and relocating the double bond between the first and second carbons to between the second and third carbons. Such, relocation of the double bond may proceed via a sigma bond metathesis. The $R_2$ substituent behaves as a leaving group in the reaction. The allylic substitution reaction mixture may contain a solvent and a base similarly as described above.

Figure 4:
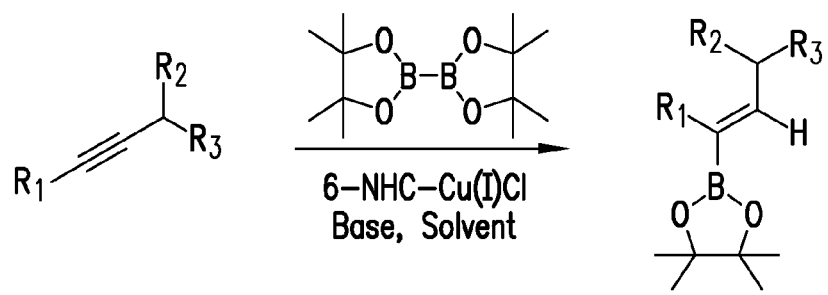
FIG. 4 is a model reaction for use of a catalyst embodiment of the present invention in a hydroboration of an alkyne substrate.

According to those embodiments in which the catalyst is used in a reaction for the hydroboration of alkynes, the substrate of the reaction may generally include molecules having a triple bond between a first carbon atom and a second carbon atom with the first carbon bonded to a first substituent or group ($R_1$; not to be confused with $R_1$ of the catalyst) and the second carbon bonded to a third carbon, which is bonded to a second substituent or group ($R_2$; not to be confused with $R_2$ of the catalyst) and a third substituent or group ($R_3$; not to be confused with $R_3$ of the catalyst). The $R_1$ substituent of the substrate may generally be any group where the atom directly attached to the double bond is a carbon, such as any alkyl group, aryl group, etc., the $R_2$ substituent of the substrate may generally be any alkyl, aryl, carbonate, siloxy, proteo, ester or aryloxy group, and the $R_3$ substituent of the substrate may generally be any group where the atom directly attached to the double bond is a carbon, such as any alkyl group, aryl group, etc. According to these embodiments as shown in FIG. 4, the hydroboration of alkynes reaction may proceed in the presence of the catalyst by bonding of a boron atom of a diboron-containing compound, such as Bis(pinacolato)diboron, Bis(catecholato)diboron, or any compound containing a boron-boron bond, to the first carbon and converting the triple bond into a double bond between the first and second carbons. The hydroboration of alkynes reaction mixture may contain a solvent and a base similarly as described above.

Having described many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

6-NHC Metal Complex Synthesis

Figure 5A:
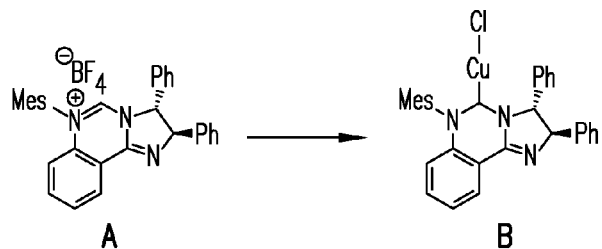
FIG. 5A is a reaction scheme showing in situ formation of a catalyst complex embodiment of the present invention (B) from a carbene precursor (A)
Figure 5B:
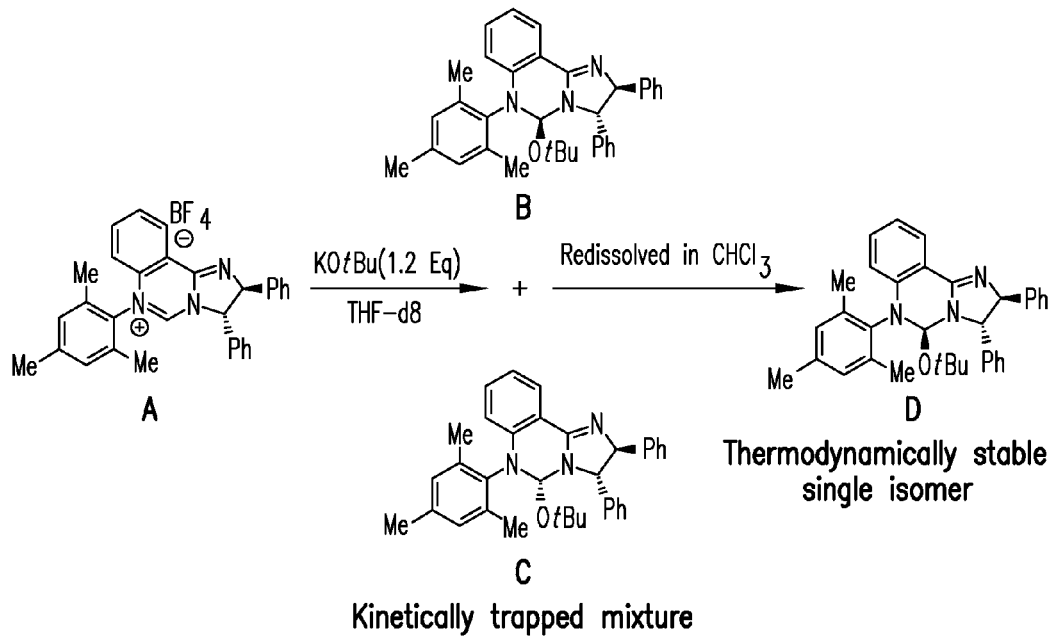
FIG. 5B is a reaction scheme showing isolated formation of a catalyst complex embodiment of the present invention (D) from a carbene precursor (A) with addition products (B and C)

The formation of a copper (I) complex of a 6-NHC ligand according to embodiments of the present invention, and its use in performing asymmetric hydroborations is described. A 6-NHC complex embodiment of the present invention (B) may be prepared in situ or as an isolated complex according to at least two methods. As shown in FIG. 5A, the in situ approach may be carried out by dissolving a carbene precursor (A) in benzene followed by the addition two equivalents of lithium hexamethyldisilazide (LiHMDS) with simultaneous addition of copper (I) chloride. This solution may turn from transparent to deep yellow. In this example, a crude NMR spectra has been shown to exhibit peaks characteristic of previously observed NHC-metal complexes. According to the isolating approach for forming a catalyst complex embodiment of the present invention (D) in FIG. 5B, the carbene precursor (A) may be treated with sodium t-butoxide in THF to generate the addition products (B and C) followed by immediate addition of CuCl. Higher yields may be obtained when the solvent is exchanged to $CH_2Cl_2$. The adduct may be cleanly changed to NHC—CuCl complex in about 12 hours through NMR experiment.

Example 2

6-NHC Metal Complex Synthesis

Figure 6:
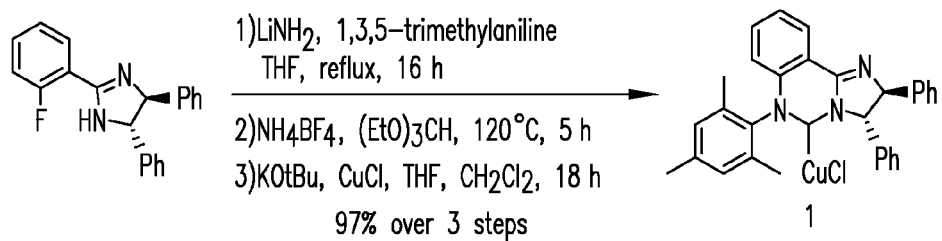
FIG. 6 is a reaction scheme for the synthesis of a 6-NHC copper chloride catalyst complex embodiment of the present invention (1) in several steps from a precursor.

A 6-NHC metal complex catalyst embodiment of the present invention may be prepared as shown in FIG. 6. Fluoroimidazoline may be synthesized via a known method, and a mesityl group may be installed using nucleophilic aromatic substitution in 99% yield. See, e.g., Busacca, C. A., et al., *Org. Lett.*, 10:341 (2008); and Davis, E. M., et al., *Org. Process Res. Dev.*, 9:843 (2005), the entire contents and disclosures of which are hereby incorporated by reference. Subsequent annulation using $NH_4BF_4$/triethyl orthoformate may then produce a carbene precursor in 95% yield. Catalyst synthesis may conclude with addition of KOtBu and CuCl to yield a bench top-stable catalyst embodiment of the present invention (1) in 98% yield.

Example 3

Synthesis of 6-NHC Copper Chloride

Figure 7:
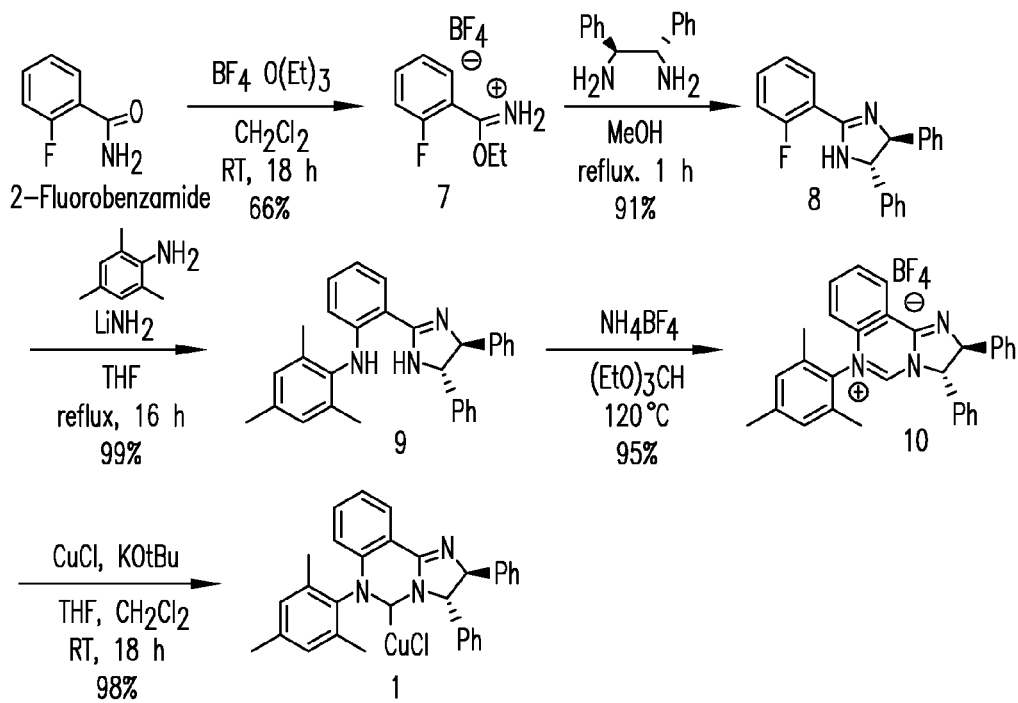
FIG. 7 is a reaction scheme for the synthesis of a 6-NHC copper chloride catalyst complex embodiment of the present invention (1) in several steps from a precursor.

See FIG. 7 for the series of reactions for this synthesis example. The synthesis of each intermediate and final 6-NHC catalyst product is described below.

Fluoroimidate (7) and Fluoroimidazoline (8)

Fluoroimidate (7) and Fluoroimidazoline (8) were synthesized according to the literature. See, e.g., Busacca, C. A. et al. (2008), supra.

N-(2-((4S,5S)-4,5-diphenyl-4,5-dihydro-1H-imidazol-2-yl)phenyl)-2,4,6-trimethylaniline (9)

Fluoroimidazoline (8) (1.13 g, 3.57 mmol) and trimethylaniline (552 µl, 3.93 mmol) were dissolved in THF (20 mL). After the addition of LiNH$_2$ (205 mg, 8.93 mmol), the mixture was heated to 80° C. The color of the reaction mixture changed to brown and ammonia gas evolved. The reaction mixture was stirred overnight. The reaction mixture was cooled to rt and quenched with sat. NH$_4$Cl solution and extracted with EtOAc and the combined organic layer was dried with Na$_2$SO$_4$. The crude product was purified by short path column chromatography (Hexane:EtOAc=20:1) to give the desired product (9) (1.53 g, 3.54 mmol) as a brownish foam in 99% yield. Rf=0.29 (Hexane:EtOAc=20:1)

(2S,3S)-6-mesityl-2,3-diphenyl-3,6-dihydro-2H-imidazo[1,2-c]quinazolin-4-ium tetrafluoroborate (10)

Aminoimidazoline (9) (810 mg, 1.88 mmol) and NH$_4$BF$_4$ (237 mg, 2.26 mmol) were added to the triethyl orthoformate (10 mL) and the mixture was heated to 120° C. After 1 h, white solid formed. The reaction mixture was stirred for an additional 4 h. After cooling to rt, Et$_2$O was added. The slurry was filtered yielding 815 mg of solid was obtained. 180 mg of solid was obtained after the filtrate was reflux to remove Et$_2$O and stirred at 50° C. overnight. The combined solid was stirred in the presence of H$_2$O and EtOAc. After phase separation, water layer was extracted again with EtOAc. The combined organic layers were dried with Na$_2$SO$_4$ and evaporated under reduced pressure. Pure product (10) (942 mg, 1.78 mmol) was obtained by recrystallization under EtOAc as a white solid in 95% yield.

((2S,3S)-6-mesityl-2,3-diphenyl-2,3,5,6-tetrahydroimidazo[1,2-c]quinazolin-5-yl)copper(I) chloride (1)

Imidazoquinazolium salt (10) (100 mg, 0.189 mmol) and CuCl (21.0 mg, 0.212 mmol) were charged into a schlenk flask and placed under high vacuum for 1 h. Anhydrous THF was added to the mixture at 0° C. KOtBu solution in THF (212 µl, 0.212 mmol, 1 M solution in THF) was added to the mixture dropwise. During the addition of KOtBu, a blue color appeared and immediately disappeared. After complete addition of KOtBu solution, the blue color maintained for ten seconds and then changed to light brown. After 10 min, THF was carefully removed under vacuum and CH$_2$Cl$_2$ was added to the reaction mixture. The reaction mixture was stirred for 18 h. The reaction mixture was filtered through Celite and washed with CH$_2$Cl$_2$. The filtrate was reduced under high vacuum. The crude product was used for asymmetric reactions without further purification. For analytically pure samples, the crude product was purified by flash column chromatography on silica gel (CH$_2$Cl$_2$ to CH$_2$Cl$_2$:EtOAc=100:1) to give the desired copper chloride complex (1) (100 mg, 0.185 mmol) as a yellow solid in 98% yield. Rf=0.20 (CH$_2$Cl$_2$:EtOAc=100:1)

Example 4

Optimization of Use & Substrate Diversity of 6-NHC Metal Catalyst in β-borylation Reactions Addition of boron across double bonds is a useful methodology that may be accomplished using a variety of metal catalysts. The conjugate addition of boron to electron poor alkenes, (β-borylation) provides access to highly functionalized intermediates useful in the construction of complex products. In general, copper-based catalysts yield faster reactions under milder conditions and with greater selectivity compared to other transition metals. See, e.g., Lawson, Y. G., et al., *Chem. Commun.*, 2051 (1997) (Pt catalyzed reactions); Ali, H. A., et al., *Organometallics*, 20:3962 (2001); Bell, N. J., et al., *Chem. Commun.*, 1854 (2004); Kabalka, G. W., et al., *Tetrahedron Lett.*, 43:2323 (2002) (Rh catalyzed reactions); Hirano, K., et al., *Org. Lett.*, 9:5031 (2007) (Ni catalyzed reactions); Ito, H., et al., *Tetrahedron Lett.*, 41:6821 (2000); Takahashi, K. et al., *J. Organomet. Chem.*, 625:47 (2001); Mun, S., et al., *Org. Lett.*, 8:4887 (2006); Lee, J.-E., et al., *Chem. Commun.*, 733 (2008); Lee, J.-E., et al., *Angew. Chem., Int. Ed.*, 47:145 (2008); Lillo, V., et al., *Organometallics*, 28:659 (2009); Sim, H.-S., et al., *Chem. Eur. J.*, 15:1939 (2009); Fleming, W. J., et al., *Org. Biomol. Chem.*, 7:2520 (2009); Schiffner, J. A., et al., *Angew. Chem., Int. Ed.*, 49:1194 (2010); and Chen, I.-H. Et al., *J. Am. Chem. Soc.*, 131:11664 (2009), the entire contents and disclosures of which are hereby incorporated by reference:

The process of copper-based catalysis in β-borylation reactions may be proposed to result from an in situ formed Cu—B species formed by exchange of a copper ligand with one borane from a diborane compound. It is speculated that the active catalyst is a Cu—B species formed by exchanging a copper alkoxide with bis(pinacolato) diboron. See, e.g., Laitar, D. S., et al., *J. Am. Chem. Soc.*, 127:17196-17197 (2005); Dang, L., et al., *Chem. Commun.*, ??:3987 (2009); Lillo, V., et al., *Dalton Trans.*, 2899 (2009); and Dang, L., et al., *Organometallics*, 27:4443 (2008), the entire contents and disclosures of which are hereby incorporated by reference. The copper bound boron then acts as a nucleophile reacting alkenes. Recently, asymmetric versions have been reported. It has been shown that commercially available bidentate phosphine ligands may provide a copper complex capable of catalyzing asymmetric hydroborations to α,β-unsaturated amides and esters with high yield and enantiomeric excess. See, e.g., Lee, J. E. et al. (2008), supra. It was demonstrated that (R)—(S)-josiphos copper (I) complexes catalyze asymmetric β-borylations to α,β-unsaturated nitriles, amides and esters with high yield and enantiomeric excess (ee). It has also been shown that five-membered ring NHC-based ligands may demonstrate excellent selectivities when they are used in hydroborating aryl-functionalized alkenes. See, e.g., Lee, K. S. et al. (2009), supra. A NHC-copper complex to hydroborylate styrenic alkenes with high yield and selectivity was used, and a method requiring only a NHC ligand to catalyze β-borylations was demonstrated. See, e.g., Lee, Y., et al., *J. Am. Chem. Soc.*, 131:3160 (2009); and Lee, K.-S. Et al., *J. Am. Chem. Soc.*, 131:7253 (2009), the entire contents and disclosures of which are hereby incorporated by reference. It has also been shown that NHC ligands may be used to catalyze hydroboration of substrates similarly to Yun, et al., but with lower selectivity. See, e.g., Lillo, V. et al. (2009), supra. Copper-N-hetereocyclic carbene (NHC) complexes were used to catalyze similar reactions but with poorer selectivity.

Figures 8A, 8B:
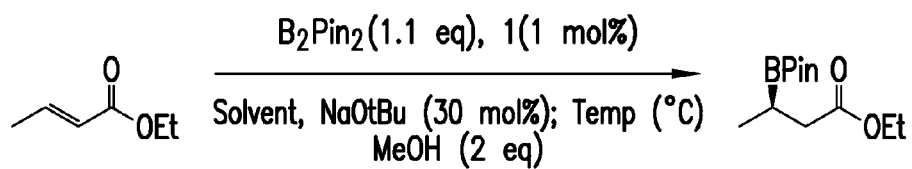
FIG. 8A is a reaction scheme for varying and optimizing reaction conditions including temperature, solvent and reaction time for a β-borylation reaction to synthesize a β-borylated ester in the presence of a catalyst complex embodiment of the present invention.
FIG. 8B is a table showing the results of experiments using different reaction conditions for a β-borylation reaction in the presence of a catalyst complex embodiment of the present invention (b—determined by $^1$H NMR of the crude material; c—determined by GC after oxidizing the boronate to alcohol by treatment with $H_2O_2$/NaOH; d—configuration was assigned by comparison to the alcohol; $B_2Pin_2$=Bis(pinacolato)diboron)

The catalyst of the present invention is shown to be a highly active and enantioselective 6-NHC catalyst. Thus far, however, no reports of carbene copper complexes are known to demonstrate high yield and enantioselectivity for β-borylation. Exploratory studies using a model β-borylation reaction (FIG. 8A) in N$_2$ atmosphere were performed to assess optimal solvent and temperature conditions for a catalyst complex embodiment of the present invention (See complex 1 in FIG. 6 or 7) to yield β-borylated products in high yield and enantioselectivity (See Table in FIG. 8B). These results reveal that this catalyst complex is highly active and provides complete consumption of starting materials within about 1 min at 0° C. with about 1 mol % of catalyst in diethyl ether to give 78% ee of the desired product (See entry 1). Further temperature screenings revealed that 86% ee could be realized at −55° C. with maintenance of useful reaction rate (See entries 2, 3). Non-polar solvents such as diethyl ether and toluene were identified as optimal solvents for the β-borylation reaction. Diethyl ether was selected for further experiments because of its easier removal.

In this example, α,β-unsaturated ester (0.20 mmol) and bis(pinacolato) diboron (56 mg, 0.22 mmol) were dissolved in Et$_2$O or toluene (1 mL). NaOtBu (6 mg, 0.060 mmol) was added to the reaction mixture. And then the reaction mixture was cooled to resulting temperature and MeOH (18 μL, 0.4 mmol) was added. After 5 min, 6-NHC copper catalyst (1.1 mg, 0.0020 mmol or 3.3 mg, 0.0060 mmol) was added. After complete consumption of α,β-unsaturated ester, the reaction mixture was filtered through silica gel and washed with Et$_2$O. The filtrate was concentrated under rotary evaporator. The resulting residue was purified by column chromatography (Hexane:EtOAc=20:1) to afford the desired products. It was found that the order of addition was critical to achieve high yields and ee's reproducibly.

For the determination of enantioselectivity, the resulting boronate was dissolved in EtOAc (2 mL) and oxidized by treatment of H$_2$O$_2$ (5 eq) and 1 M NaOH solution (5 eq) for 30 min. After phase separation, the organic layer was evaporated under high vacuum. The crude alcohol product was purified by column chromatography.

Figures 9A, 9B:
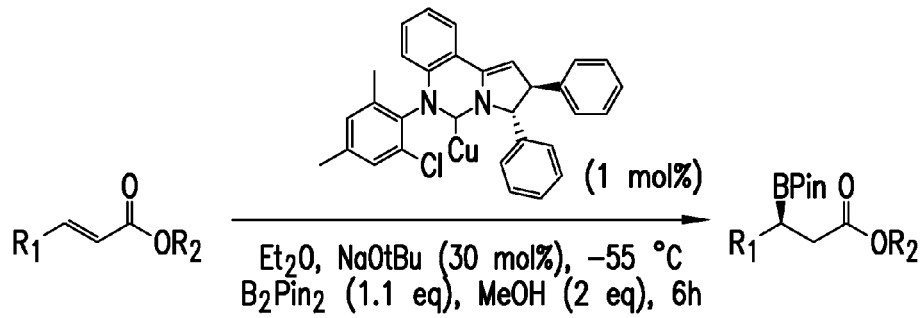
FIG. 9A is a general reaction scheme for testing the scope of substrates for β-borylation in the presence of a catalyst complex embodiment of the present invention.
FIG. 9B is a table showing the results of β-borylation reactions according to FIG. 8A with a variety of different substrates in terms of yield and enantiomeric excess (ee) (b—isolated yields; c—determined by GC after oxidizing the boronate to alcohol by treatment with $H_2O_2$/NaOH; d—solvent is toluene; e—3 mol % calatyst is used; f—reactions run at −30° C.; g—ee of i-butyl ester)

With optimized conditions established for the model reaction, the β-borylation in N$_2$ atmosphere of a variety of other substrates in the presence of a 6-NHC catalyst complex was investigated (See FIG. 9A). The catalyst complex embodiment of the present invention demonstrated success at transforming a variety of aliphatic and aromatic α-β unsaturated esters to β-borylated products in high yield and enantioselectivity (See Table in FIG. 9B). Linear aliphatic substrates such as ethyl hexenoate and ethyl octenoate had high enantioselectivities (90% and 91%, respectively) (entries 2 and 3), Increased γ-branching was also well tolerated, (entries 4-6). Interestingly methyl cinnamate gave the highest ee (87% ee) among the methyl, ethyl and isobutyl esters of cinnamic acid, which is opposite to the aliphatic esters (entries 1, 7). We were surprised to find that the o-methyl substituted cinnamate esters showed selectivity similar to the aliphatic esters, with the isobutyl ester giving higher ee (96%) than ethyl ester (92%, entry 9).

Figure 10:
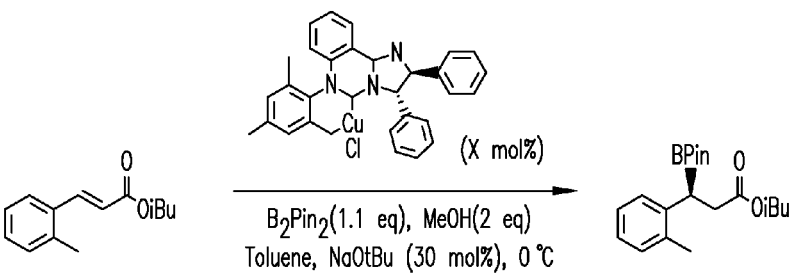
FIG. 10 is a reaction scheme and table showing the results of β-borylation reactions to test catalyst loading under varied reaction conditions including substrate concentration, Mol % of catalyst and reaction time (a—0.2 M concentration; b—0.4 M concentration; c—0.8 M concentration; d—conversion measured by GC)

To better quantify the activity of catalyst complex embodiment, we reduced the catalyst loading for the reaction as shown in the Table in FIG. 10. Even at about 0.01 mol % of the catalyst complex, the reaction proceeded in high yield and high enantioselectivity and still took place within about 100 min (See entry 5). Though NHC catalysts are known to provide very high turnover numbers (TONs), an asymmetric case with the activity presented in the Table in FIG. 10 is unfamiliar. See, e.g., Mayr et al., supra.

In the example summarized in FIG. 10, catalyst loading experiments were set up using standard reaction conditions except the concentration of the reaction mixture and the catalyst loading were varied as illustrated in the table above. Reaction progress was monitored by GC chromatography and complete consumption of the starting material in the times are indicated in FIG. 10. We confirmed there was less than 1% of starting material by examining product $^{13}$C satellites in relationship to residual starting material peaks (no starting material peaks were observed) in the reaction mixture by $^1$H NMR. Based on this information, we concluded that the conversion is >99%.

Figure 11A:
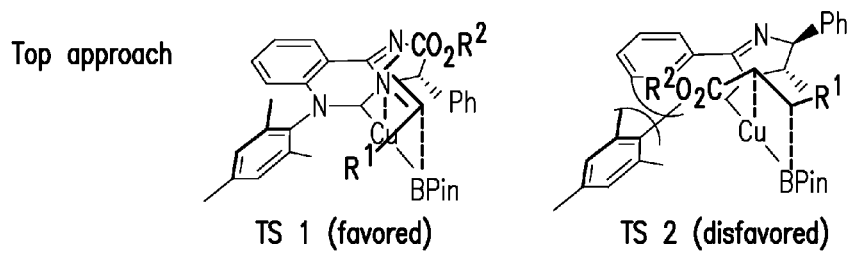
FIG. 11 is a scheme showing a possible model for the transition state of a catalyst complex embodiment of the present invention.
Figure 11B:
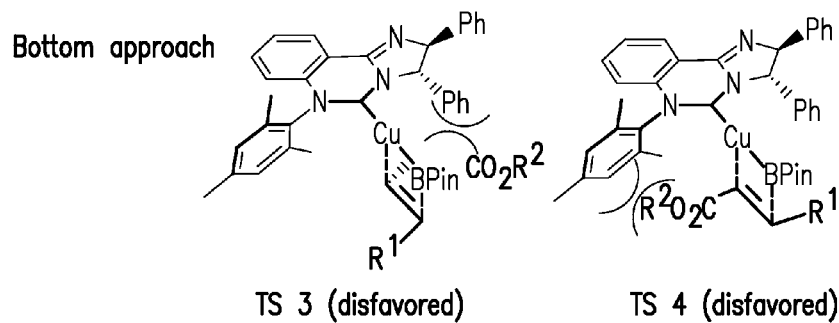

DFT calculations have provided insight for the mechanistic model shown in FIG. 11. See, e.g., Dang et al., supra. It is proposed that the α,β-unsaturated ester could approach the Cu—B complex from four different orientations as shown in FIG. 11. The "bottom approach" is blocked by the imidazoline's phenyl group (TS 3) and the mesityl group (TS 4). In the "top approach," TS 1 is free from steric repulsion whereas TS 2 forces the substrate ester and mesityl group to collide. In summary, we have developed a new, six membered annulated NHC copper complex that catalyzes β-borylations with high yield and enantioselectivity. The catalyst is very active showing 10,000 turnovers at 0.01 mol % of catalyst without significant decrease of enantioselectivity and with useful reaction rates. Further studies concerning the mechanism and the expansion of reaction scope may be undertaken.

Example 5

Reactions for Chemoselectivity Comparisons of Catalyst in β-borylation

Figure 12A:
FIG. 12A shows the structures of a catalyst embodiment of the present invention (1) and other catalysts (2,3) for comparison.

The enantioselectivity of the a catalyst embodiment of the present invention (See complex 1 in FIG. 12A) in a β-borylation reaction is compared to other catalysts (See 2, 3 in FIG. 12A). The results including the ratio of 5a/5b with these catalyst comparisons are summarized in the table in FIG. 12E.

Figure 12B:
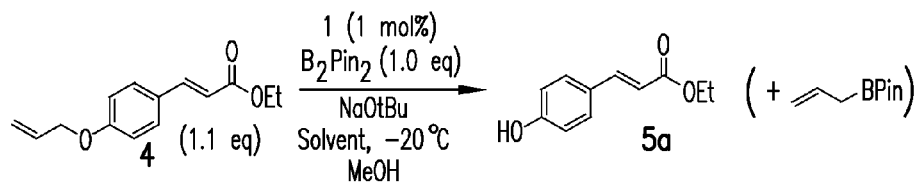
FIG. 12B is a β-borylation reaction for testing the enantioselectivity of a catalyst embodiment of the present invention (1)

FIG. 12B shows the reaction to test the catalyst embodiment of the present invention (1). In this example, compound 4 (51 mg, 0.22 mmol) and bis(pinacolato) diboron (51 mg, 0.20 mmol) were dissolved in Et$_2$O (1 mL). NaOtBu (6 mg, 0.060 mmol) was added to the reaction mixture. And then the reaction mixture was cooled down to −20° C. and MeOH (18 μL, 0.40 mmol) was added. After 5 min, 6-NHC copper catalyst (1) (1.1 mg, 0.0020 mmol) was added. After complete consumption of bis(pinacolato) diboron, the reaction mixture was filtered through silica gel and washed with Et$_2$O. The filtrate was concentrated under rotary evaporator. $^1$H NMR of crude product was taken for the determination of the ratio of deallylated product to borylated product (5a/5b=>25/1). The resulting residue was purified by column chromatography (Hexane:EtOAc=6:1 to 4:1) to afford the desired products, 5a (27 mg, 70% yield).

Figure 12C:
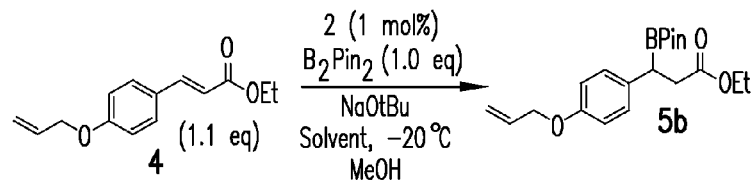
FIG. 12C is a β-borylation reaction for testing the enantioselectivity of another catalyst (2) for comparison.

FIG. 12C shows a comparison reaction to test and compare another catalyst (2). In this example, compound 4 (51 mg, 0.22 mmol) and bis(pinacolato) diboron (51 mg, 0.20 mmol) were dissolved in Et$_2$O (1 mL). NaOtBu (6 mg, 0.060 mmol) was added to the reaction mixture. And then the reaction mixture was cooled down to −20° C. and MeOH (18 μL, 0.40 mmol) was added. After 5 min, 5-NHC copper catalyst (2) (0.8 mg, 0.0020 mmol) was added. After complete consumption of bis(pinacolato) diboron, the reaction mixture was filtered through silica gel and washed with Et$_2$O. The filtrate was concentrated under rotary evaporator. $^1$H NMR of crude product was taken for the determination of the ratio of deallylated product to borylated product (5a/5b=<1/24). The resulting residue was purified by column chromatography (Hexane:EtOAc=50:1 to 20:1) to afford the desired products, 5b (51 mg, 71% yield).

Figure 12D:
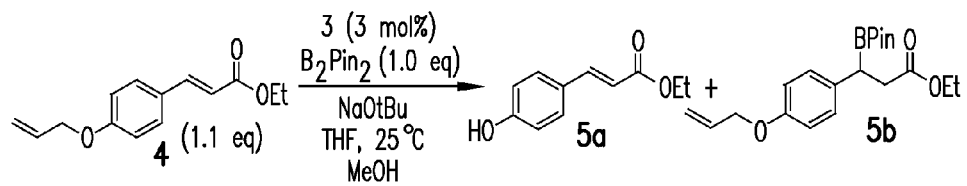
FIG. 12D is a β-borylation reaction for testing the enantioselectivity of another catalyst (3) for comparison.

FIG. 12D shows a comparison reaction to test and compare another catalyst (3). In this example, xantphos (8.7 mg, 0.015 mmol), CuCl (1.5 mg, 0.015 mmol) and NaOtBu (4.3 mg, 0.045 mmol) were dissolved in THF (0.4 mL) and the reaction mixture was stirred for 30 min. Bis(pinacolato) diboron (127 mg, 0.50 mmol) were added to the reaction mixture. After 3 min, stirring, compound 4 (128 mg, 0.55 mmol) solution in THF (1.6 mL) was added to the reaction mixture, followed by the addition of MeOH (45 µL, 1.0 mmol). After complete consumption of bis(pinacolato) diboron, the reaction mixture was filtered through silica gel and washed with Et$_2$O. The filtrate was concentrated under rotary evaporator. $^1$H NMR of crude product was taken for the determination of the ratio of deallylated product to borylated product (5a/5b=1/1.5). The resulting residue was purified by column chromatography (Hexane:EtOAc=8:1 to 6:1) to afford the desired products, 5a (17 mg, 16% yield).

Example 6

Validation of Reaction Condition for Xantphos Catalyzed Reaction

We tried to reproduce the β-borylation reaction of ethyl cinnamate using another group's reaction conditions. See, e.g., Mun, S. et al. (2006), supra. The same results were observed as reported. However, when ethyl 4-hydroxy cinnamate was tested, there was a significantly lower yield. It is proposed that the aromatic hydroxyl group disrupts the active catalytic species. See table in FIG. 13.

Example 7

Reactions for Chemoselectivity Comparisons of Catalyst in Allylic Substitution

The enantioselectivity of the a catalyst embodiment of the present invention (See complex 1 in FIG. 12A) in a allylic substitution reaction is compared to other catalysts (See 2, 3 in FIG. 12A). The results including the ratio of 6a/6b with these catalyst comparisons are summarized in the table in FIG. 14D. Linear product (6b) was synthesized and confirmed by comparison with known data. See, e.g., Godeau, J., et al., *Electrochim. Acta,* 54:5116 (2009), the entire contents and disclosure of which is hereby incorporated by reference. Peaks of 6b in GC chromatogram in these examples for 1 or 2 catalyzed allylic substitution reaction were not observed.

FIG. 14A shows the reaction to test the catalyst embodiment of the present invention (1). In this example, (E)-(hex-2-enyloxy)benzene (35 mg, 0.20 mmol) and bis(pinacolato) diboron (57 mg, 0.22 mmol) were dissolved in Et$_2$O (1 mL). NaOtBu (6 mg, 0.060 mmol) was added to the reaction mixture. And then the reaction mixture was cooled down to 0° C. and MeOH (18 µL, 0.40 mmol) was added, followed by the addition of cyclooctane solution (100 µL, 1.0 M in Et$_2$O). After 5 min, 6-NHC copper catalyst (1) (1.1 mg, 0.0020 mmol) was added. The reaction was monitored by GC according to the time and GC yield was determined by the calibration of area ratio between product peak and internal standard (cyclooctane) peak. After 20 min, the reaction mixture was filtered through silica gel and washed with Et$_2$O. The filtrate was concentrated under rotary evaporator. The resulting residue was purified by column chromatography (Hexane) to afford the desired products, (37 mg, 86% yield).

FIG. 14B shows the reaction to test and compare another catalyst (2). In this example, (E)-(hex-2-enyloxy)benzene (35 mg, 0.20 mmol) and bis(pinacolato) diboron (57 mg, 0.22 mmol) were dissolved in Et$_2$O (1 mL). NaOtBu (6 mg, 0.060 mmol) was added to the reaction mixture. And then the reaction mixture was cooled down to 0° C. and MeOH (18 µL, 0.40 mmol) was added, followed by the addition of cyclooctane solution (100 µL, 1.0 M in Et$_2$O). After 5 min, 5-NHC copper catalyst (2) (0.8 mg, 0.0020 mmol) were added. The reaction was monitored by GC according to the time and GC yield was determined by the calibration of area ratio between product peak and internal standard (cyclooctane) peak. The reaction was carried out until no conversion was detected.

FIG. 14C shows the reaction to test and compare another catalyst (3). In this example, xantphos (8.7 mg, 0.015 mmol), CuCl (1.5 mg, 0.015 mmol) and NaOtBu (4.3 mg, 0.045 mmol) were dissolved in THF (0.4 mL) and the reaction mixture was stirred for 30 min. Bis(pinacolato) diboron (127 mg, 0.50 mmol) were added to the reaction mixture. After 3 min, stirring, (E)-(hex-2-enyloxy)benzene (88 mg, 0.50 mmol) solution in THF (1.6 mL) was added to the reaction mixture, followed by the addition of cyclooctane solution (100 µL, 1.0 M in Et$_2$O) and MeOH (45 µL, 1.0 mmol). The reaction was monitored by GC according to the time and GC yield was determined by the calibration of area ratio between product peak and internal standard (cyclooctane) peak. The reaction was carried out until no conversion was detected.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A compound having a first, second and third fused rings and the following structural formula:

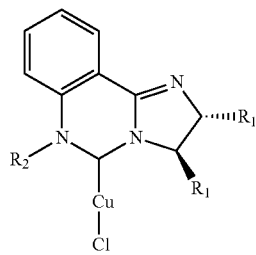

wherein each R$_1$ group bound to the third ring is one of the following: alkyl, vinyl, allyl, alkynyl or aryl,
wherein the R$_2$ group bound to the second ring is one of the following: alkyl, vinyl, allyl, alkynyl or aryl, and
wherein the carbon atom positioned between the nitrogens of the second ring and bonded to Cu is a carbene atom.

2. The compound of claim 1, wherein each R$_1$ group is aryl.

3. The compound of claim 2, wherein each R$_1$ group is phenyl.

4. The compound of claim 1, wherein R$_2$ is aryl.

5. The compound of claim 4, wherein R$_2$ is a radical group having the following formula:

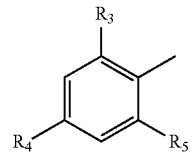

wherein each of the radical groups R$_3$, R$_4$, and R$_5$ are alkyl.

6. The compound of claim 5, wherein two members of the group consisting of $R_3$, $R_4$ and $R_5$ are the same and the third member of the group is different from the two members of the group that are the same.

7. The compound of claim 6, wherein $R_3$ and $R_5$ are each methyl.

8. The compound of claim 5, wherein $R_3$, $R_4$ and $R_6$ are different from each other.

9. A composition comprising the compound of claim 1.

10. The composition of claim 9, further comprising a non-polar solvent.

11. The composition of claim 10, wherein the non-polar solvent is one or more of the following: diethyl ether, toluene, THF, or $CH_2Cl_2$.

12. The composition of claim 9, further comprising a polar aprotic solvent.

13. The composition of claim 12, wherein the polar aprotic solvent is $CH_3CN$, DMF or DMSO.

14. The composition of claim 9, further comprising a base, wherein the base is an alkoxide or nitrogenous base.

15. The composition of claim 9 further comprising a substrate for a β-functionalization reaction.

16. The composition of claim 15, wherein the β-functionalization reaction is a β-borylation reaction, β-silylation reaction or β-phosporylation reaction.

17. The composition of claim 16, wherein the substrate is a molecule having a double bond between two carbon atoms, wherein one of those carbons is bonded to an electron withdrawing group (EWG) and the other carbon is bonded to a variable substituent or group.

18. The composition of claim 17, wherein the variable substituent or group of the substrate is any group having a carbon atom directly bonded to the carbon of the double bond.

19. The composition of claim 17, wherein the EWG of the substrate is one or more of the following: an ester, carboxylic acid, acid halide, amide, sulfone, nitro, nitrile, thioester, or thioamide.

20. The composition of claim 16, further comprising a compound having a boron-boron bond.

21. The composition of claim 9, further comprising a substrate for an allylic substitution reaction.

22. The composition of claim 21, wherein the substrate is a molecule having a double bond between a first carbon atom and a second carbon atom, wherein the first carbon bonded to a first variable substituent or group and the second carbon bonded to a third carbon, and wherein the third carbon is bonded to a second variable substituent or group.

23. The composition of claim 22, wherein the first variable substituent or group is any group having a carbon atom directly bonded to the carbon of the double bond.

24. The composition of claim 22, wherein the second variable substituent or group is a carbonate or aryloxy group.

25. The composition of claim 9, further comprising a substrate for a hydroboration of alkynes reaction.

26. The composition of claim 25, wherein the substrate is a molecule having a triple bond between a first carbon atom and a second carbon atom, wherein the first carbon atom is bonded to a first variable substituent or group and the second carbon atom is bonded to a third carbon, and wherein the third carbon is bonded to a second variable substituent or group and a third variable substituent or group.

27. The composition of claim 26, wherein the first variable substituent or group is any group having a carbon atom directly bonded to the carbon of the double bond.

28. The composition of claim 26, wherein the second variable substituent or group is an alkyl, aryl, carbonate, siloxy, proteo, ester or aryloxy group, and the third variable substituent or group is an alkyl or aryl group.

29. A compound having a first, second and third fused rings and the following structural formula:

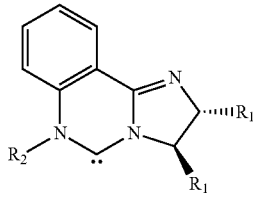

wherein each $R_1$ group bound to the third ring is one of the following: alkyl, vinyl, allyl, alkynyl or aryl, wherein the $R_2$ group bound to the second ring is one of the following: alkyl, vinyl, allyl, alkynyl or aryl, and wherein the symbol

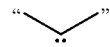

represents a carbene atom.

30. The compound of claim 29, wherein each $R_1$ group is aryl.

31. The compound of claim 30, wherein each $R_1$ group is phenyl.

32. The compound of claim 29, wherein $R_2$ is aryl.

33. The compound of claim 32, wherein $R_2$ is a radical group having the following formula:

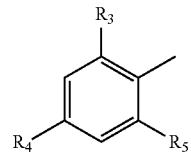

wherein each of the radical groups $R_3$, $R_4$, and $R_5$ are alkyl.

34. The compound of claim 33, wherein two members of the group consisting of $R_3$, $R_4$ and $R_5$ are the same and the third member of the group is different from the two members of the group that are the same.

35. The compound of claim 34, wherein $R_3$ and $R_5$ are each methyl.

36. The compound of claim 33, wherein $R_3$, $R_4$ and $R_6$ are different from each other.

* * * * *